US00PP33141P2

(12) United States Plant Patent
Misato et al.

(10) Patent No.: US PP33,141 P2
(45) Date of Patent: Jun. 8, 2021

(54) ***MANDEVILLA* PLANT NAMED 'SUNPA 4411'**

(50) Latin Name: *Mandevilla hybrida*
Varietal Denomination: Sunpa 4411

(71) Applicants: Tomoya Misato, Shiga (JP); Masahiro Yamada, Shiga (JP)

(72) Inventors: Tomoya Misato, Shiga (JP); Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 16/974,012

(22) Filed: Sep. 5, 2020

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Mandevilla* plant named 'Sunpa 4411', characterized by its compact plant habit; vigorous growth habit; freely branching habit; early and freely flowering habit; long flowering period; and vivid purplish red-colored flowers with vivid yellow-colored throats.

1 Drawing Sheet

Botanical designation: *Mandevilla hybrida.*
Cultivar denomination: 'SUNPA 4411'.

BACKGROUND OF THE INVENTION

The present invention relates to a new and distinct cultivar of *Mandevilla* plant, botanically known as *Mandevilla hybrida* and hereinafter referred to by the name 'Sunpa 4411'.

The new *Mandevilla* plant is a product of a planned breeding program conducted by the Inventors in Higashiomi, Shiga, Japan. The objective of the breeding program is to create new compact and freely branching *Mandevilla* plants with freely flowering habit and attractive flowers.

The new *Mandevilla* plant originated from an open-pollination in Higashiomi, Shiga, Japan in May, 2013 of a proprietary selection of *Mandevilla hybrida* identified as code number 10MB29-4, not patented, as the female, or seed parent with an unknown proprietary selection of *Mandevilla hybrida* as the male, or pollen, parent. The new *Mandevilla* plant was discovered and selected by the Inventor as a single flowering plant from within the progeny of the stated open-pollination in a controlled greenhouse environment in Higashiomi, Shiga, Japan in September, 2014.

Asexual reproduction of the new *Mandevilla* plant by terminal vegetative cuttings in Higashiomi, Shiga, Japan since March, 2015 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 4411'. These characteristics in combination distinguish 'Sunpa 4411' as a new and distinct *Mandevilla* plant:

1. Compact plant habit.
2. Vigorous growth habit.
3. Freely branching habit.
4. Early and freely flowering habit.
5. Long flowering period.
6. Vivid purplish red-colored flowers with vivid yellow-colored throats.

Plants of the new *Mandevilla* can be compared to plants of the female parent selection. Plants of the new *Mandevilla* differ primarily from plants of the female parent selection in flower color as plants of the new *Mandevilla* have vivid purplish red-colored flowers with vivid yellow-colored throats whereas plants of the female parent selection have pale pink-colored flowers. In addition, plants of the new *Mandevilla* have shorter internodes than plants of the female parent selection.

Plants of the new *Mandevilla* can be compared to plants of the *Mandevilla hybrida* 'Sunmandecripi', disclosed in U.S. Plant Pat. No. 18,578. In side-by-side comparisons, plants of the new *Mandevilla* differ from plants of 'Sunmandecripi' in the following characteristics:

1. Plants of the new *Mandevilla* are shorter and have shorter internodes than plants of 'Sunmandecripi'.
2. Leaves of plants of the new *Mandevilla* are decussate whereas leaves of plants of 'Sunmandecripi' are opposite.
3. Leaves and leaf petioles of plants of the new *Mandevilla* are darker green in color than leaves and leaf petioles of plants of 'Sunmandecripi'.

4. Petal apices of plants of the new *Mandevilla* are rounded whereas peal apices of plants of 'Sunmandecripi' are acuminate.
5. Plants of the new *Mandevilla* have smaller calyxes than plants of 'Sunmandecripi'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet is a side perspective view of a typical flowering plant of 'Sunpa 4411' grown in a container.

The photograph at the bottom of the sheet is a close-up view of a typical flower of 'Sunpa 4411'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 4411'.

Parentage:

*Female, or seed, parent*.—Proprietary selection of *Mandevilla hybrida* identified as code number 10MB29-4, not patented.

*Male, or pollen, parent*.—Unknown proprietary selection of *Mandevilla hybrida*, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact and semi-climbing plant habit; vigorous growth habit; freely branching habit; suitable for hanging baskets and garden plantings.

*Lateral branch description*.—Length: About 8.9 cm. Diameter: About 3.7 mm. Internode length: About 6.9 cm. Strength: Strong, flexible. Texture: Smooth, glabrous. Color, developing: Close to 144B; moderately tinged with close to 173B and 175A. Color, fully developed: Close to 199A.

Leaf description:

*Arrangement and quantity*.—Decussate, simple; about 17 leaves per lateral branch.

*Length*.—About 7.4 cm.

*Width*.—About 4.4 cm.

*Shape*.—Elliptic.

*Apex*.—Acuminate.

*Base*.—Cordate.

*Margin*.—Entire; slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 137B. Developing leaves, lower surface: Close to 147C. Fully expanded leaves, upper surface: Close to NN137A; venation, close to 145B. Fully expanded leaves, lower surface: Close to 147B; venation, close to 145C.

*Petioles*.—Length: About 1.4 cm. Diameter: About 1.7 mm. Texture, upper and lower surfaces: Smooth, glabrous. Color, upper and lower surfaces: Close to 145A.

Flower description:

*Flower type and habit*.—Single salverform flowers arranged in axillary racemes; flowers face upright to outwardly; freely flowering habit with about four to six flowers per inflorescence and about 79 flowers developing per plant.

*Natural flowering season*.—Early flowering habit, plants begin flowering about six weeks after planting; long flowering period, plants flower continuously from summer until late autumn in Japan.

*Flower longevity on the plant*.—About seven to ten days; flowers not persistent.

*Fragrance*.—None detected.

*Flower buds*.—Height: About 6.6 cm. Diameter: About 1.2 mm. Shape: Rhombic. Color: Close to 53C.

*Flowers*.—Appearance: Salverform; flared trumpet, corolla fused and five-parted; flowers roughly star-shaped. Diameter: About 7.1 cm. Depth (length): About 6.1 cm. Throat diameter: About 1.6 cm. Tube length: About 2.2 cm. Tube diameter, proximally: About 2.7 mm.

*Corolla*.—Quantity and arrangement: Five petals arranged in a single whorl and fused towards the base into an elongated tube; petal lobes not imbricate. Petal lobe length: About 3 cm. Petal lobe width: About 2.7 cm. Petal lobe shape: Obovate, moderately asymmetrical. Petal lobe apex: Rounded. Petal lobe margin: Entire; slightly undulate; not recurved. Petal lobe texture and luster, upper surface: Smooth, glabrous; matte. Petal lobe texture and luster, lower surface: Smooth, glabrous; glossy. Throat texture: Smooth, glabrous. Tube texture: Smooth, glabrous. Color: Petal lobe, when opening, upper surface: Close to between 53C and N57A; towards the base, close to N57B. Petal lobe, when opening, lower surface: Close to 58B; towards the right margin, close to 53B; cental line, close to 58D. Petal lobe, fully opened, upper surface: Close to N57A; towards the base, close to N57C; color becoming closer to N57B to N57D with development. Petal lobe, fully opened, lower surface: Close to 57D; towards the right margin, close to 53D; cental line, close to 62C. Throat: Proximally, close to 15A and distally, close to N57C and 15B; at the petal lobe, close to 65D; venation, close to 15C. Tube: Proximally, close to 154D and distally, close to 58B; venation, similar to tube colors.

*Calyx*.—Quantity and arrangement: Five sepals arranged in a single whorl, fused at the base; calyx, star-shaped. Sepal length: About 4.8 mm. Sepal width: About 1.9 mm. Sepal shape: Lanceolate. Sepal apex: Acuminate. Sepal margin: Entire. Sepal texture, upper and lower surfaces: Smooth, glabrous. Sepal color, upper surface: Close to 145C; towards the base, close to 145B; towards the margins and apex, tinged with close to N34C. Sepal color, lower surface: Close to 145B.

*Peduncles*.—Length: About 4.7 cm. Diameter: About 1.9 mm. Texture: Smooth, glabrous. Aspect: Upright to outwardly. Color: Close to 144B.

*Pedicels*.—Length: About 1.4 cm. Diameter: About 1.6 mm. Texture: Smooth, glabrous. Aspect: Upright to outwardly. Color: Close to 144B.

*Reproductive organs*.—Stamens: Quantity and arrangement: Typically five; filaments fused to corolla; anthers, connivent. Anther size: About 1.6 mm by 7.5 mm. Anther shape: Lanceolate. Anther color: Close to 10B. Pollen amount: None observed. Pistils: Quantity: Typically one. Pistil length: About 2.8 cm. Style color: Close to 145C. Stigma shape: Globose. Stigma color: Close to 160B. Ovary color: Close to 145B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 4411' as illustrated and described.

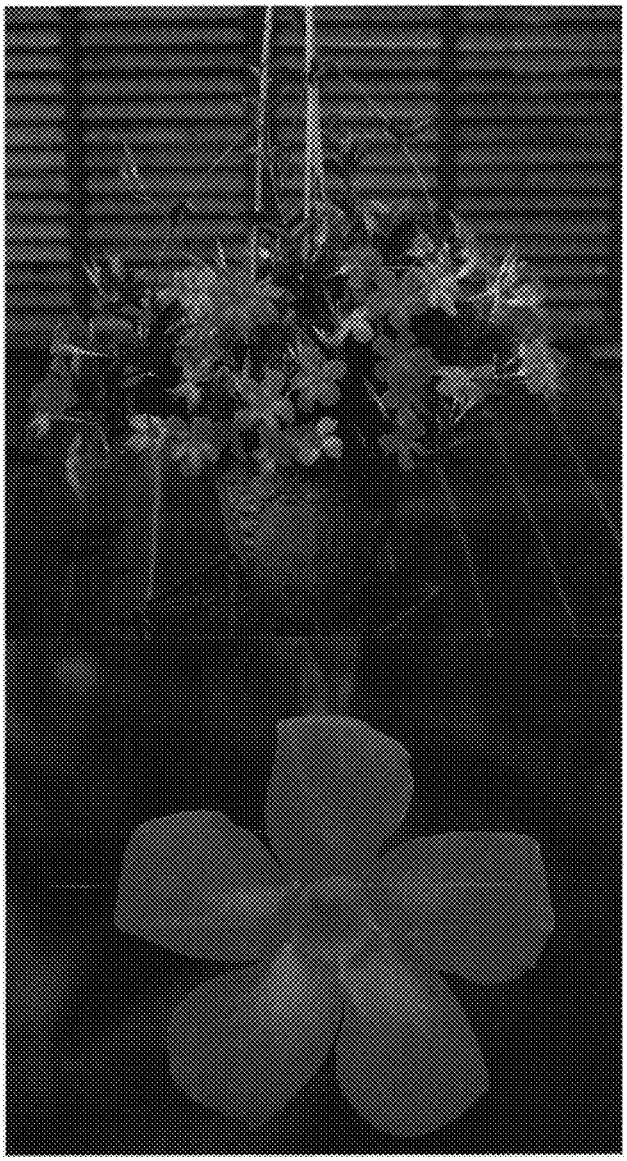

* * * * *